United States Patent
Sarkela et al.

(10) Patent No.: US 6,950,698 B2
(45) Date of Patent: Sep. 27, 2005

(54) METHOD OF POSITIONING ELECTRODES FOR CENTRAL NERVOUS SYSTEM MONITORING

(75) Inventors: Mika Sarkela, Helsinki (FI); Hanna Viertio-Oja, Espoo (FI)

(73) Assignee: Instrumentarium Corp. (FI)

(*) Notice: Subject to any disclaimer, the term of this patent is extended or adjusted under 35 U.S.C. 154(b) by 44 days.

(21) Appl. No.: 10/612,828

(22) Filed: Jul. 2, 2003

(65) Prior Publication Data

US 2005/0004489 A1 Jan. 6, 2005

(51) Int. Cl.$^7$ .................................................. A61B 5/04
(52) U.S. Cl. .................................................. 600/544
(58) Field of Search ................................. 600/544, 545

(56) References Cited

U.S. PATENT DOCUMENTS

| | | | |
|---|---|---|---|
| 5,291,888 A | | 3/1994 | Tucker |
| 5,479,934 A | * | 1/1996 | Imran ........................ 600/544 |
| 5,491,492 A | | 2/1996 | Knapp et al. |
| 5,772,591 A | * | 6/1998 | Cram ......................... 600/383 |
| 6,032,065 A | * | 2/2000 | Brown ........................ 600/383 |
| 6,233,472 B1 | * | 5/2001 | Bennett et al. ............. 600/383 |
| 6,394,953 B1 | | 5/2002 | Devlin et al. |
| 6,625,481 B2 | * | 9/2003 | Bennett et al. ............. 600/383 |
| 6,654,632 B2 | * | 11/2003 | Lange et al. ................ 600/544 |
| 2003/0055355 A1 | | 3/2003 | Viertio-Oja |

FOREIGN PATENT DOCUMENTS

| | | |
|---|---|---|
| WO | WO-93/02616 | 2/1993 |
| WO | WO-02/00096 | 1/2002 |
| WO | WO 03/003916 A1 | 1/2003 |
| WO | 03/003916 | 1/2003 |

OTHER PUBLICATIONS

Patent Abstracts of Japan, vol. 0175, No. 61 (C–1119), Oct. 8, 1993 & JP 5–161621 A (The Sailor Pen Co. Ltd.), Jun. 29, 1993 Abstract.

* cited by examiner

Primary Examiner—Robert L. Nasser
Assistant Examiner—Navin Natnithithadha
(74) Attorney, Agent, or Firm—Andrus, Sceales, Starke & Sawall, LLP

(57) ABSTRACT

Method of positioning electrodes in an electrode array, comprising at least five or at least seven electrodes for central nervous system (CNS) monitoring from the forehead of a patient's head. The electrodes of the array are optimally located for discriminating EEG, FEMG and EM components from the recorded biopotential signals.

26 Claims, 4 Drawing Sheets

METHOD OF POSITIONING ELECTRODES FOR CENTRAL NERVOUS SYSTEM MONITORING

BACKGROUND OF THE INVENTION

The present invention relates to a method for central nervous system (CNS) monitoring, and more specifically to a method of positioning electrodes in an electrode array comprising at least five or at least seven electrodes for monitoring central nervous system with the help of electroencephalography (EEG), frontal electromyography (FEMG) and eye movement (EM) signals from the forehead of a patient's head. The invention also relates to a method of sensing pain reactions of a patient.

Electroencephalography (EEG) is a well-established method for assessing the brain function by picking up the weak signals generated in the brain with electrodes on the skull surface. To obtain the signals, multiple electrodes are placed on the scalp of a patient in accordance with a recognized protocol. EEG has been in wide use for decades in basic research of the neural system of brain as well as clinically in diagnosis of various neurophysiological disorders.

In a traditional EEG measurement electrodes are attached following the standard 10-20 system. Said system has been used by neurophysiologists for decades to record EEG and to find pathological EEG changes. The system however requires cumbersome attachment of multiple electrodes, especially when the electrodes are attached in the hair environment.

One of the special applications for EEG, which has received attention to during the 1990's is use of a processed EEG signal for objective quantification of the amount of brain activity for the purpose of determining the level of consciousness of a patient. In its simplest form, the usage of EEG allows for the automatic detection of the alertness of an individual, ie. if he or she is awake or asleep. This has become a significant issue, both scientifically and commercially, in the context of measuring the depth of unconsciousness induced by anesthesia during surgery. Modern anesthesia practices use a sophisticated balancing technique with a combination of drugs for maintaining adequate hypnosis, analgesia, muscle relaxation, and/or suppression of the autonomic nervous system and blockage of the neuromuscular junction. The need for a reliable system for monitoring of the adequacy of the anesthesia is based on both safety and economical concerns. An anesthesia dose, which is too light can, in the worst case, cause the patient to wake up during the operation and to create a highly traumatic experience both for the patient and for the personnel administering the anesthesia. At the opposite extreme, the administration of too deep anesthesia generates increased costs due to the excessive use of anesthesia drugs and the time needed to administer the drugs. Over dosage of the anesthetic drugs also affects the quality and length of the post-operative period immediately after the operation and the time required for any long-term post-operative care.

In the anesthesia and the intensive care said 10-20 system is cumbersome to use. This is because these environments are already crowded by many other measuring systems, such as blood pressure, ECG, inspired and expired gas measurements. The additional labour-consuming measuring system would take too much time and effort from the care personnel. There is even though need for central nervous system monitoring needs in these areas. The consciousness level of the patient is varied in both of said environments and till today there has not been a practical method for monitoring the level of consciousness in the anesthesia and the intensive care environment.

As told before in the anesthesia environment patient is anesthetized with hypnotic, analgesic and neuromuscular blocking agents. The neuromuscular blocking agents, given in a certain extent block the neuromuscular junction and the patient looses ability to move herself or himself. This can create a situation where patient feels pain but cannot communicate. Without central nervous system monitoring there is a risk of giving too little or too much anesthetics. If too little hypnotic drugs are given to the patient he or she could awake during operation, which could cause traumatic experience especially for the patient and also for the personnel.

Another important issue about the use of EEG is defining the level of sedation in Intensive Care Units (ICU). However, the situation in ICU is a little bit more complicated than in Operating Rooms (OR). In ICU patient is sedated by sedatives, which means that he or she is usually at the higher level of consciousness that in anesthesia. Sedatives are usually same medicines as anesthetics, but the doses are lighter. Sedatives have usually both hypnotic and analgesic components, but neuromuscular blocking agents are very rarely used in ICU. Without central nervous system monitoring patients are usually over sedated, which leads to longer treatment periods. Sedation induces amnesia, which afterwards often causes physiological problems to the patients. This is because of gap in memory.

Because neuromuscular blocking agents are not often used during sedation patients are able to move themselves when feeling pain. So patient might be agitated and he or she might be eg. fighting against ventilator, which cause huge amount of artifacts to the processed signal. If patient is not agitated he or she might be alert about surroundings, so patient can eg. move his or her eyes, which causes eye movement (EM) artifacts to the EEG. It is essentially important to identify those artifacts and reject contaminated signal periods from further EEG signal processing. Also patients in ICU might have neurological disorders, eg. status epilepticus, hydrocephalus, brain tumor or subarachnoidal hemorrage (SAH). This causes irrelevancies and non-symmetries to EEG. It is important to detect these phenomena without delay to ensure proper treatment of the patient.

The above mentioned reasons have generated commercial efforts to develop EEG devices to said environments during the past ten years. The main requirements for such monitoring can be described by the following features, ease of use, reliability and good quality. The efforts in this area have concentrated into reliable and easy-to-use electrodes as well as to good quality signal processing.

A significant main advancement in making EEG-based measurement of the adequacy of anesthesia or sedation an easy-to-use routine was a finding based on Positron Emission Tomography (PET) that determined that the effects of the anesthetic drugs on the brain are global in nature. This means that for many applications it is enough to measure the forebrain or frontal cortex EEG from the forehead of the patient. The forehead is both an easy to access and hairless location on the patient. Electrodes placed with an appropriate spacing between the electrodes on the forehead can pick up an adequate signal originating from the anterior cortex in the brain.

Since the Positron Emission Tomography (PET) studies have shown that the anesthesia effect is a global phenomenon in the brain, the sensor development efforts have concentrated on the hairless frontal area of the head. The first commercial sensor for this application area was developed by the company Aspect Medical Systems, Inc. U.S. Pat. No. 6,032,064 can be mentioned as an example of the art describing the sensor developed by Aspect Medical Systems, Inc. The company mentioned above also has patented many electrode configurations relating to placement of the electrodes on frontal and temple areas of the patient's head. Reference is made here to U.S. Pat. No. 6,394,953.

While the foregoing has discussed the use of EEG signals, it is also desirable to obtain frontal electromyographic (FEMG) signals arising from the forehead of the patient. The frontalis muscle is the first indicator of approaching consciousness. When this muscle activity is sensed by appropriately placed electrodes it provides an early indication that the patient is emerging from anesthesia. Similarly these electrodes can sense pain reactions when the anesthesia is not adequate, for example because of inadequate analgesia. So the FEMG signals give an early warning of arousal and may also indicate inadequate analgesia.

During sedation information from FEMG is essential to assess optimal level of sedation. In optimally sedated patients frontalis muscle responses to noxious stimuli, but if sedation is too deep frontalis muscle is unresponsive. To assess optimal level of sedation information about patient level of consciousness is also needed, meaning that simultaneous processing of EEG and FEMG signals must be performed. Because spectrums of EEG and FEMG signals overlap discrimination of signals requires sophisticated algorithms or optimal electrode position on the forehead.

SUMMARY OF THE INVENTION

The object of the invention is to provide a simple and practical method of positioning an electrode array so that the electrodes of the array are optimally located for discriminating EEG, FEMG and EM components from the recorded biopotential signals.

An advantage of the invention is that the method is extremely simple, practical and reliable, and therefore optimal measuring results can be obtained. Another advantage of the invention is in that the method can be materialized very simply, ie. by using a simple electrode array, whereby costs can be kept at reasonably low level.

BRIEF DESCRIPTION OF THE DRAWINGS

In the following the invention will be described in greater detail by means of the examples shown in the drawing, in which.

DETAILED DESCRIPTION OF THE INVENTION

Figure 1:
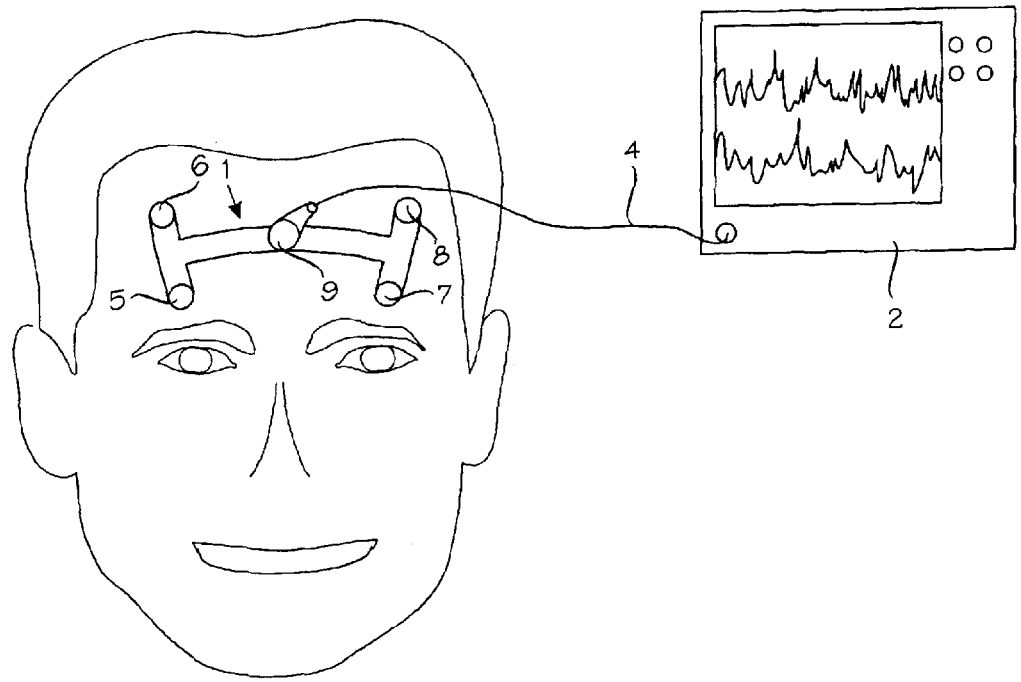
FIG. 1 shows a frontal view of a human head in which electrodes are positioned according to the first embodiment of the invention.

Referring now to the Figures in which corresponding details in different embodiments have been marked with same reference numerals. As shown in FIG. 1 the system according to the present invention comprises an electrode array 1 connected to a monitor 2 by a cable 4. The electrode array 1 has been attached onto the forehead of the patient as shown in FIG. 1. The electrode array 1 transmits biopotential signals from the forehead of the patient to the monitor 2, which carries out signal processing and displays EEG, FEMG and EM data in desired form. The data obtained can also be stored for future use.

The electrode array 1 shown in FIG. 1 comprises five electrodes, ie. the first electrode 5, the second electrode 6, the third electrode 7, the fourth electrode 8 and the fifth electrode 9.

The first electrode 5 and the third electrode 7 are used to detect phasic and tonic activation of facial muscles intended for expression of painful mimic responses (corrugator, procerus, frontalis and orbicularis oculi muscles), the FEMG signal. The first and the second electrodes detect also some EEG related signal. The second electrode 6 and the fourth electrode 8 are used to detect cortical activity (EEG) of frontal lobe from the hairless fronto-lateral area and only some FEMG related signal. The fifth electrode 9 is a ground electrode.

According to the basic idea of the invention the first electrode 5 is positioned above an eyebrow of the patient near frontalis and orbicularis muscles, advantageously directly above an eyebrow in vertical line with the eye. The second electrode 6 is positioned to the same cortical hemisphere as the first electrode 5. However the second electrode 6 is positioned above the first electrode 5 advantageously as far as possible from the first electrode 5 on the hairless fronto-lateral area of the patient. The third electrode 7 is positioned directly above the other eyebrow, when compared to the first electrode 5, in vertical line with the eye. The third electrode 7 is thus positioned at the opposite hemisphere when compared to the first electrode 5. The fourth electrode 8 is positioned to the same cortical hemisphere as the third electrode 7. However the fourth electrode 8 is positioned above the third electrode 7 advantageously as far as possible from the third electrode 7 on the hairless fronto-lateral area of the patient. The fifth electrode 9 can be positioned to any area of the patient advantageously having bone immediately under the skin, for example on the forehead area or on the area behind an ear of the patient. It is also advantageous to place the electrodes of a hairless area of the patient's skin. In the embodiment of FIG. 1 the fifth electrode is positioned at the centre of the forehead of the patient. It is very advantageous to place the fifth electrode 9 essentially at the centre of the area defined by the four other electrodes 5, 6, 7 and 8. This gives an opportunity to optimize Common Mode Rejection Ratio (CMRR) of the measured signal.

Figure 3:
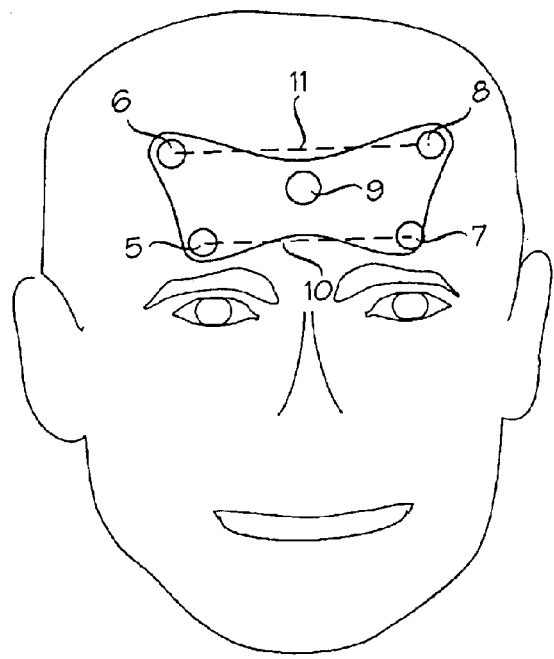
FIG. 3 shows a first operating principle of the first embodiment of the invention.

The five-electrode system described above and placed according to the basic idea of the present invention offers two different principles of operation to measure biopotential signals from the patient. Said two principles are shown in montages shown in FIGS. 3 and 4. The first montage shown in FIG. 3 offers a simple solution to distinguish EEG, FEMG and EM signals from each other. A biopotential with relatively strong FEMG component is measured between the first electrode 5 and the second electrode 7, which is called the FEMG channel 10. A biopotential with relatively strong EEG component is measured between the second electrode 6 and the fourth electrode 8, which is called the EEG channel 11. The EEG and FEMG components can be identified from the two signals for example by spectral analysis. Eye movements in all directions have identical morphology in both channels, but they contribute to higher amplitudes in the FEMG channel. Eye movements can be detected and removed for example by analyzing the correlation between the two channels.

Figure 4:
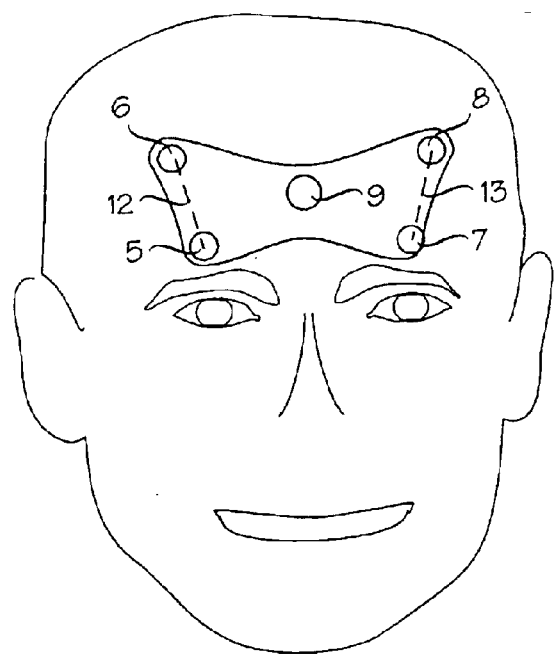
FIG. 4 shows a second operating principle of the first embodiment of the invention.

The second montage shown in FIG. 4 offers a choice to measure the biopotential signals from both cortical hemispheres for functional comparison. The measurement may provide diagnostic information to detect brain injuries and epileptic discharges of critical care patients. The first biopotential signal 12 is measured between the first electrode 5 and the second electrode 6, and the second biopotential signal 13 is measured between the third electrode 7 and the fourth electrode 8. In both channels EEG and FEMG signals are superimposed on top of each other. Horizontal and vertical eye movements have identical morphology in both channels, whereas diagonal eye movements have different morphologies. The second montage shown in FIG. 4 is therefore somewhat less sensitive in detecting eye movements then the first montage shown in FIG. 3. The second montage does not discriminate between EEG and FEMG components as accurately as the first montage.

There is also a possibility to switch between the montages with help of the system described in PCT document WO 03/003916 A1. The first montage is optimized to assess the level of sedation and the second montage is purposeful to detect non-symmetries between hemispheres, which indicates brain injuries or epileptic discharges. One solution might be eg. to switch between the montages in every five minutes. Another possibility is to use the first montage and switch to the second montage only when brain injuries or epileptic discharges are present. The second montage is then purposeful to localize phenomena.

Figure 2:
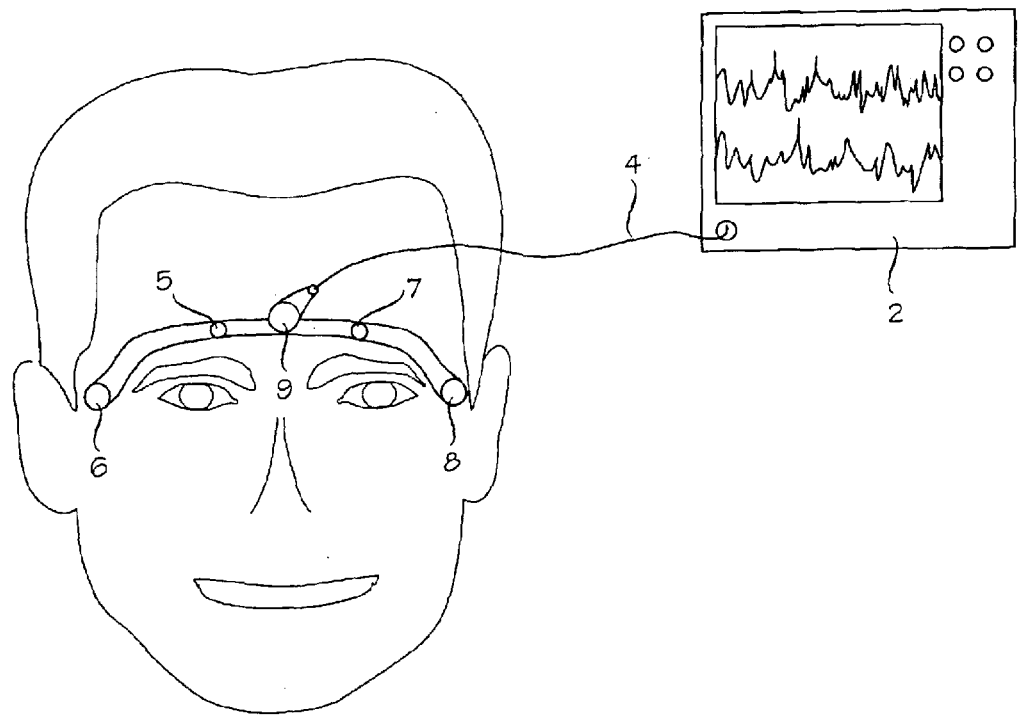
FIG. 2 shows a frontal view of a human head in which electrodes are positioned according to the second embodiment of the invention.

The second embodiment of the present invention includes also a solution to identify directions of the eye movements. The second embodiment is shown in FIG. 2. In the second embodiment the second electrode 6 is positioned to the temple of the patient for example to the area between an eye and an ear advantageously at eye level anterior to an ear, at the same side of the head as the first electrode 5. The first electrode 5 and the third electrode 7 are positioned in the same way as described in connection with the first embodiment of the invention described in FIG. 1. The fourth electrode 8 is positioned to the temple of the patient for example to the area between an eye and an ear advantageously at eye level anterior to an ear at the same side of the head as the third electrode 7. In said electrode configuration EEG, FEMG and EM signals are measured with two bipolar montages shown in FIG. 5. The first electrode 5 and the second electrode 6 are used to measure EEG from one hemisphere 14, the first electrode is a positive pole and the second electrode is a negative pole. The third electrode 7 and the fourth electrode 8 are used to measure EEG from the other hemisphere 15. The third electrode is a positive pole and the fourth electrode is a negative pole. Both bipolar montages measure also FEMG and EM. In the embodiment of FIG. 2 the fifth electrode 9, ie. the ground electrode, is placed at the middle area between the first 5 and the third electrode 7. The fifth electrode 9 can however be placed otherwise too, for example in the way as described in connection with FIG. 1.

Figure 5:
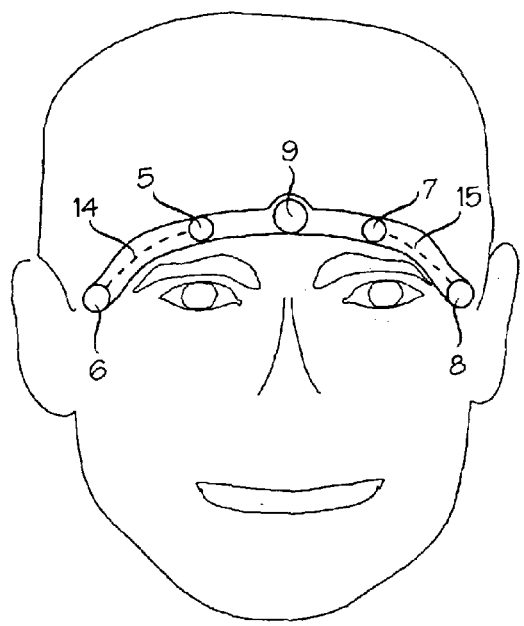
FIG. 5 shows an operating principle of the second embodiment of the invention.

With the arrangement shown in FIG. 5 it is possible to discriminate vertical horizontal and diagonal eye movements from each other. Eye can be modeled as an electrical dipole. Cornea has positive charge and retina has negative charge. When a patient watches up positive charge flows to the forehead, otherwise when a patient watches down negative charge flows to the forehead. When a patient blinks his or her eyes, there is a sudden rise and fall on the voltage at the forehead. This is because eyelid conducts the positive charge of cornea.

Vertical eye movements (VEM) including eye blinks generate identical VEM-signal morphologies to both channels. Horizontal eye movements (HEM) generates identical but reversed potential HEM-signal morphologies to both channels. Biopotential signals originating from diagonal eye movements (DEM) depend on the direction of DEMs according to table below. After eye movements are identified, it is possible to define their velocity. This is also interesting property, because velocity of the eye movements correlates with the vigilance level of the patient. Vigilance is probably correlated with the level of consciousness.

| Type of EM | Direction | Effect to voltage on left channel | Effect to voltage on right channel |
| --- | --- | --- | --- |
| VEM | Up | Up | Up |
|  | Down | Down | Down |
| HEM | Right to left | Up | Down |
|  | Left to right | Down | Up |
| DEM | Down left to up right | Up | No effect |
|  | Up left to down right | No effect | Down |
|  | Down right to up left | No effect | Up |
|  | Up right to down left | Down | No effect |

Figure 6:
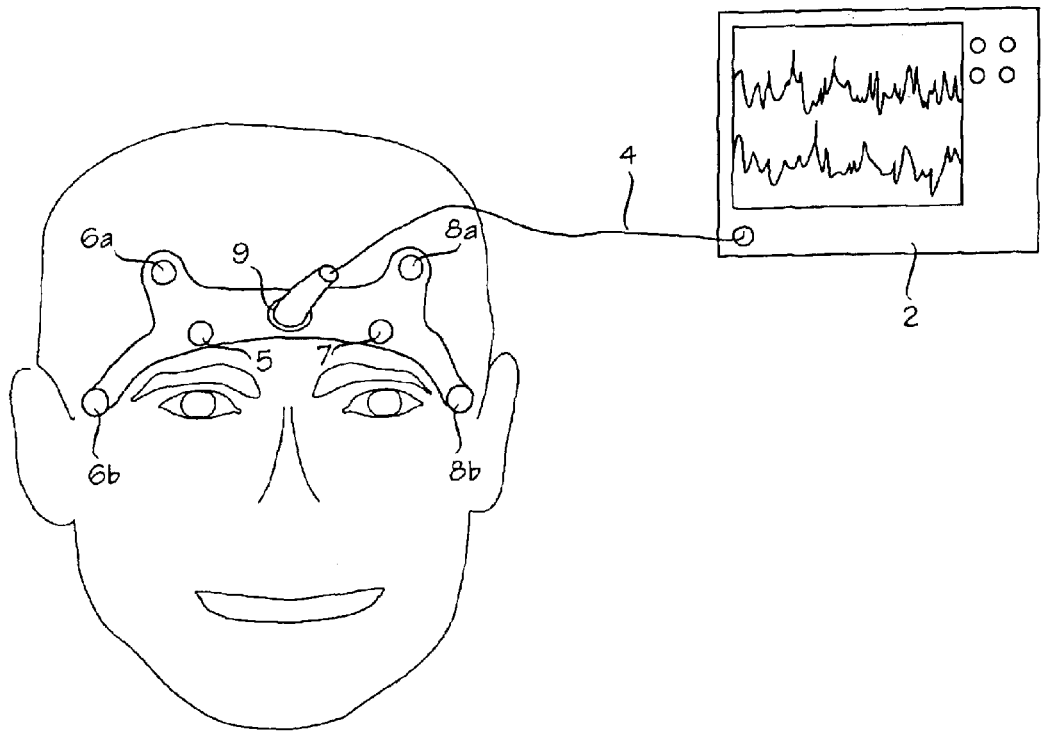
FIG. 6 shows a frontal view of a human head in which the electrodes are positioned according to the third embodiment of the invention.

According to the basic idea of the invention it is also possible to combine the embodiments of FIG. 1 and FIG. 2. This combination, ie. the third embodiment of the invention is shown in FIG. 6. In FIG. 6 corresponding details in different embodiments have been marked with same reference numerals as in FIGS. 1 and 2. In this embodiment the first electrode, the third electrode and the fifth electrode (ground electrode) are marked with the same reference numerals as in FIGS. 1 and 2. Said electrodes 5, 7 and 9 are placed in the same way as described in connection with FIG. 1.

The embodiment shown in FIG. 6 uses an array of seven electrodes. Location of the electrodes are those described in connection with. FIGS. 1 and 2. In the embodiment shown the second electrode is marked with a reference number 6a and the sixth electrode is marked with a reference number 6b. The fourth electrode is marked with a reference number 8a and the seventh electrode is marked with a reference number 8b. The second electrode 6a corresponds to the second electrode 6 of the embodiment shown in FIG. 1 and the sixth electrode 6b corresponds to the second electrode 6 shown in the embodiment of FIG. 2. The fourth electrode 8a corresponds to the fourth electrode 8 of the embodiment shown in FIG. 1 and the seventh electrode corresponds to the fourth electrode 8 of FIG. 2. The system shown in FIG. 6 is a combination of the systems shown in FIGS. 1 and 2. The fifth electrode, ie. the ground electrode is placed at the centre of the area defined by the first 5, the second 6a, the third 7 and the fourth electrode 8a in the embodiment of FIG. 6. The fifth electrode can however be otherwise too in the way as described in connection with FIGS. 1 and 2.

Figure 7:
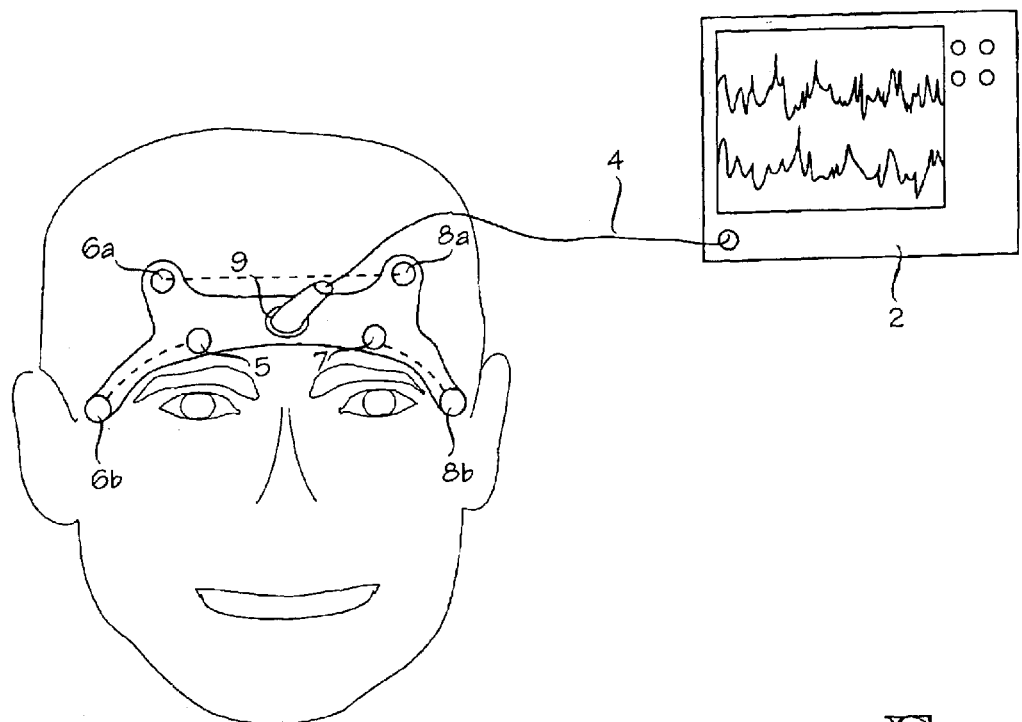
FIG. 7 shows a first operating principle of the third embodiment of the invention, and FIG. 8 shoes a second operating principle of the third embodiment of the invention.
Figure 8:
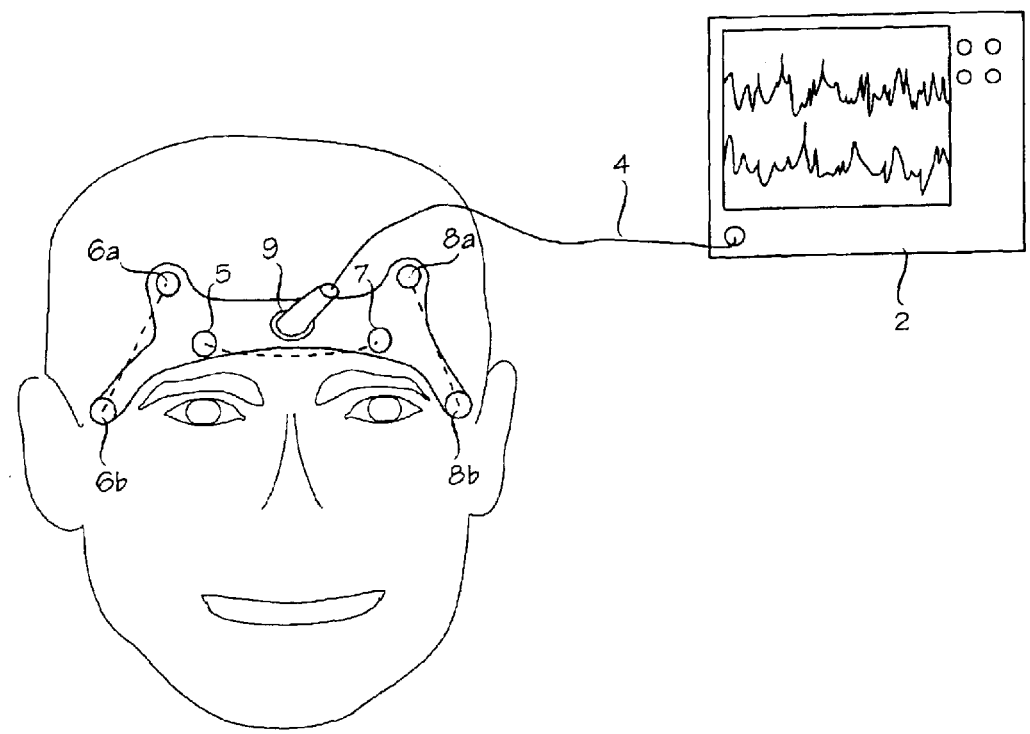

The seven-electrode system described above and shown in FIG. 6 offers different montages to measure biopotential signals from the patient. It is easy to understand that this embodiment offers the montages already discussed in connection with the embodiments of FIGS. 1 and 2. The main advantage of the embodiment of FIG. 6 is that it offers all of the benefits discussed with the embodiments of FIGS. 1 and 2 simultaneously, switching between montages is not necessary needed. FIG. 7 shows one possible montage in phantom lines. Bipolar montage between electrodes 6a and 8a is used to measure EEG. Bipolar montages between electrodes 5 and 6b and between electrodes 7 and 8b are used to measure EMG and eye movements and to identify nonsymmetries between hemispheres. FIG. 8 shows another possible montage in phantom lines. Bipolar montage between electrodes 5 and 7 is used to measure EMG. Bipolar montages between electrodes 6a and 6b and between electrodes 8a and 8b are used to measure EEG and eye movements and to identify nonsymmetries between hemispheres. There is also a possibility according to the existing needs to switch between the montages presented in FIGS. 7 and 8 or some not presented montage included in the embodiment of FIG. 6 in the way as discussed above in connection with the first and the second embodiment of the invention.

The embodiments described above are not intended to restrict the invention but only to clarify the basic idea of the invention. It is quite clear that details can be varied within the scope of the claims. It is for example within the basic idea of the invention quite possible to add one or more electrodes to the arrays described above in order to obtain some other important data of the patient if needed etc.

What is claimed is:

1. Method of positioning electrodes in an electrode array comprising at least five electrodes for central nervous system (CNS) monitoring from the forehead of a patient's head, the method comprising the steps of:
    positioning a first electrode above the eyebrows to sense a signal from the frontalis and at least one of the corrugator, procerus, and orbicularis muscles of the patient and to detect phasic and tonic activation of facial muscles expressing painful mimic responses;
    positioning a second electrode above the first electrode on the fronto-lateral area of the frontal lobe of the patient and on the same hemisphere as the first electrode;
    positioning a third electrode above the eyebrows to sense a signal from the frontalis and at least one of the corrugator, procerus and orbicularis muscles of the patient at the opposite hemisphere when compared to the first electrode and to detect phasic and tonic activation of facial muscles expressing painful mimic responses;
    positioning a fourth electrode above the third electrode on the fronto-lateral area of the frontal lobe of the patient and on the same hemisphere as the third electrode; and
    positioning a fifth electrode on the patient's skin;
    wherein the at least five electrodes are arranged to distinguish at least two electroencephalography, frontal electromyography and eye movement signals from each other and assess a level of patient sedation.

2. The method of claim 1 wherein the second electrode is positioned as far as possible from the first electrode and the fourth electrode is positioned as far as possible from the third electrode.

3. The method of claim 2 wherein the areas on which the second, the fourth and the fifth electrode are positioned are hairless areas.

4. The method of claim 1 wherein the fifth electrode is positioned on the area of the patient's skin having bone immediately under the skin.

5. The method of claim 4 wherein the areas on which the second, the fourth and the fifth electrode are positioned are hairless areas.

6. The method of claim 1, wherein the first, second, third and fourth electrodes are measuring electrodes and the fifth electrode is a ground electrode.

7. The method of claim 6, wherein frontal electromyography is measured with bipolar connection between the first and the third electrode.

8. The method of claim 6, wherein electroencephalography is measured with bipolar connection between the second and the fourth electrode.

9. The method of claim 6, wherein electroencephalography from one hemisphere is measured between the first and the second electrode, and electroencephalography from the other hemisphere is measured between the third and the fourth electrode.

10. The method of claim 1 wherein the fifth electrode is positioned on the head area of the patient.

11. The method of claim 10 wherein the fifth electrode is positioned at the center of the area defined by the above mentioned four electrodes.

12. Method of positioning electrodes in an electrode array comprising at least five electrodes for central nervous system (CNS) monitoring from the forehead of a patient's head, the method comprising the steps of:
    positioning a first electrode above the eyebrows to sense a signal from the frontalis and at least one of the corrugator, procerus and orbicularis muscles of the patient and to detect phasic and tonic activation of facial muscles expressing painful mimic responses;
    positioning a second electrode to the temple of the patient at the same side of the head as the first electrode;
    positioning a third electrode above the eyebrows to sense a sign from the frontalis and at least one of the corrugator, procerus and orbicularis muscles of the patient at the opposite hemisphere when compared to the first electrode and to detect phasic and tonic activation of facial muscles expressing painful mimic responses;
    positioning a fourth electrode to the temple of the patient at the same side of the head as the third electrode; and
    positioning a fifth electrode on the patient's skin,
    wherein the at least five electrodes are arranged to measure biopotential signals from both cortical hemispheres for functional comparison to detect nonsymmetries between the hemispheres, and to detect eye movements.

13. The method of claim 12 wherein the temple is the area between an eye and an ear.

14. The method of claim 13 wherein the area is at eye level anterior of the ear.

15. The method of claim 12 wherein the fifth electrode is positioned on the area of the patient's skin having bone immediately under the skin.

16. The method of claim 15 wherein the fifth electrode is positioned on the head area of the patient.

17. The method of claim 16 wherein the fifth electrode is positioned at the middle area between the first and the third electrode.

18. The method of claim 12 wherein electroencephalography is measured from one hemisphere by using the first and the second electrode, and electroencephalography is measured from the other hemisphere by using the third and the fourth electrode.

19. The method of claim 12, wherein vertical, horizontal and diagonal eye movements are distinguished from each other.

20. Method of positioning electrodes in an electrode array comprising at least seven electrodes for central nervous system (CNS) monitoring from the forehead of a patient's head, the method comprising the steps of:

positioning a first electrode above the eyebrows to sense a signal from the frontalis and at least one of the corrugator, procerus and orbicularis muscles of the patient and to detect phasic and tonic activation of facial muscles expressing painful mimic responses;

positioning a second electrode above the first electrode on the fronto-lateral area of the frontal lobe of the patient and on the same hemisphere as the first electrode;

positioning a third electrode above the eyebrows to sense a signal from the frontalis and at least one of the corrugator, procerus and orbicularis muscles of the patient at the opposite hemisphere when compared to the first electrode and detect phasic and tonic activation of facial muscles expressing painful mimic responses;

positioning a fourth electrode above the third electrode on the fronto-lateral area of the frontal lobe of the patient and on the same hemisphere as the third electrode;

positioning a fifth electrode on the patient's skin;

positioning a sixth electrode to the temple of the patient at the same side of the head as the first electrode; and positioning a seventh electrode to the temple of the patient's head at the same side of the head as the third electrode, wherein the at least seven electrodes are arranged to distinguish at least two of electroencephalography, frontal electromyography and eye movement signals from each other, and to measure biopotential signals from both cortical hemispheres for functional comparison to detect non-symmetries between the hemispheres, and to detect eye movements.

21. The method of claim 20 wherein the temple is the area between an eye and an ear.

22. The method of claim 21 wherein the area is at eye level anterior of the ear.

23. The method of claim 20 wherein the fifth electrode is positioned on the area of the patient's skin having bone immediately under the skin.

24. The method of claim 23 wherein the fifth electrode is positioned on the head area of the patient.

25. The method of claim 24 wherein the fifth electrode is positioned at the centre area defined by the first, the second, the third and the fourth electrodes.

26. The method of claim 20, wherein vertical, horizontal and diagonal eye movements are distinguished from each other.

* * * * *